(12) United States Patent
Karlsson et al.

(10) Patent No.: US 10,617,474 B2
(45) Date of Patent: Apr. 14, 2020

(54) SYSTEM AND METHOD FOR OPTIMIZING AN IMPLANT POSITION IN AN ANATOMICAL JOINT

(71) Applicant: Episurf IP-Management AB, Stockholm (SE)

(72) Inventors: Anders Karlsson, Kävlinge (SE); Richard Lilliestråle, Stockholm (SE)

(73) Assignee: Episurf IP-Management AB, Stockholm (SE)

( * ) Notice: Subject to any disclaimer, the term of this patent is extended or adjusted under 35 U.S.C. 154(b) by 0 days.

(21) Appl. No.: 15/853,620

(22) Filed: Dec. 22, 2017

(65) Prior Publication Data
US 2018/0177600 A1    Jun. 28, 2018

Related U.S. Application Data

(63) Continuation-in-part of application No. PCT/EP2016/082455, filed on Dec. 22, 2016.

(51) Int. Cl.
*A61B 34/10*    (2016.01)
*A61F 2/32*    (2006.01)
(Continued)

(52) U.S. Cl.
CPC ............... *A61B 34/10* (2016.02); *A61F 2/32* (2013.01); *A61F 2/38* (2013.01); *A61F 2/40* (2013.01);
(Continued)

(58) Field of Classification Search
CPC ... A61B 34/20; A61B 34/10; A61B 2034/108; A61B 2034/105; A61B 2034/107;
(Continued)

(56) References Cited

U.S. PATENT DOCUMENTS 5,692,117 A * 11/1997 Berend ................. G06T 11/001
                                                        345/475
7,239,908 B1    7/2007 Alexander et al.
(Continued)

FOREIGN PATENT DOCUMENTS

AU    2015203808 A1    7/2015
EP      2389905 A1    11/2011
(Continued)

OTHER PUBLICATIONS

International Search Report and Written Opinion dated Mar. 14, 2018, International Patent Application No. PCT/EP2017/084439, filed Dec. 22, 2017, 16 pages.

*Primary Examiner* — Ajay Ojha
(74) *Attorney, Agent, or Firm* — Davis Wright Tremaine LLP

(57) ABSTRACT

In accordance with one or more embodiments herein, a system for optimizing a position of an implant having an individually customized implant hat and at least one implant protrusion extending from the implant hat in the direction of an implant axis in an anatomical joint of a patient is provided. The system comprises a storage media and a processor which is configured to: receive medical image data representing a three dimensional image of the joint from the storage media; obtain a three dimensional virtual model of the joint which is based on the received medical image data; identify damage in the joint based on the received medical image data and/or the three dimensional virtual model of the joint; define an implant area that covers at least a major part of the identified damage; position a virtual implant template having an implant hat corresponding to said implant area in the three dimensional virtual model of the joint; and generate a customized top surface of the implant hat to correspond to a simulated healthy cartilage surface. The processor is configured to position the (Continued)

virtual implant template by: placing the virtual implant template so that the cross section area of the implant hat in a direction perpendicular to the implant axis covers at least a major part of the damage; and optimizing the tilt of the implant axis, while maintaining the position of the cross section area of the implant hat in the joint, by minimizing at least one of the maximum penetration depth into the bone along the circumference of the implant hat; the total volume of bone and/or cartilage to be removed for implanting the implant; and/or the surface area of the implant penetration into the bone.

16 Claims, 11 Drawing Sheets

(51) Int. Cl.
| | | |
|---|---|---|
| *A61F 2/38* | (2006.01) | |
| *A61F 2/40* | (2006.01) | |
| *A61F 2/42* | (2006.01) | |
| *G06T 19/20* | (2011.01) | |
| *A61F 2/30* | (2006.01) | |
| *G06T 7/00* | (2017.01) | |

(52) U.S. Cl.
CPC ................ *A61F 2/42* (2013.01); *G06T 19/20* (2013.01); *A61B 2034/102* (2016.02); *A61B 2034/104* (2016.02); *A61B 2034/105* (2016.02); *A61B 2034/107* (2016.02); *A61B 2034/108* (2016.02); *A61F 2/30756* (2013.01); *A61F 2002/3013* (2013.01); *A61F 2002/30878* (2013.01); *G06T 7/0012* (2013.01); *G06T 2207/30008* (2013.01); *G06T 2219/2004* (2013.01)

(58) Field of Classification Search
CPC ............. A61B 2034/101; A61B 17/154; A61F 2002/30952; A61F 2/4657
See application file for complete search history.

(56) References Cited

U.S. PATENT DOCUMENTS

| | | |
|---|---|---|
| 8,062,302 B2 | 11/2011 | Lang et al. |
| 2003/0216669 A1* | 11/2003 | Lang .................... A63B 5/4528 600/587 |
| 2006/0247790 A1 | 11/2006 | McKay |
| 2007/0276224 A1 | 11/2007 | Lang et al. |
| 2007/0276501 A1 | 11/2007 | Betz et al. |
| 2009/0222014 A1 | 9/2009 | Bojarski et al. |
| 2009/0226068 A1 | 9/2009 | Fitz et al. |
| 2011/0087332 A1 | 4/2011 | Bojarski et al. |
| 2011/0152869 A1 | 6/2011 | Ek et al. |
| 2012/0271417 A1 | 10/2012 | Ek |
| 2013/0211531 A1 | 8/2013 | Steines et al. |
| 2014/0244220 A1* | 8/2014 | McKinnon ................ A61F 2/02 703/1 |
| 2014/0276873 A1* | 9/2014 | Meridew ............... A61F 2/4609 606/91 |
| 2015/0230874 A1 | 8/2015 | Musuvathy et al. |
| 2016/0331467 A1* | 11/2016 | Slamin .................. A61B 34/10 |

FOREIGN PATENT DOCUMENTS

| | | |
|---|---|---|
| WO | 2007092841 A2 | 8/2007 |
| WO | 2008098061 A2 | 8/2008 |
| WO | 2009108591 A1 | 9/2009 |
| WO | 2010099357 A1 | 9/2010 |
| WO | 2016004991 A1 | 1/2016 |
| WO | 2016005542 A1 | 1/2016 |

* cited by examiner

SYSTEM AND METHOD FOR OPTIMIZING AN IMPLANT POSITION IN AN ANATOMICAL JOINT

CROSS-REFERENCE TO RELATED APPLICATION

This application is a continuation-in-part of PCT Application No. PCT/EP2016/082455, filed Dec. 22, 2016, entitled "SYSTEM AND METHOD FOR OPTIMIZING AN IMPLANT POSITION IN AN ANATOMICAL JOINT," the content of which is incorporated by reference herein.

TECHNICAL FIELD

The present disclosure relates generally to systems and methods for optimizing an implant position in an anatomical joint of a patient.

BACKGROUND

Surgical implants have since long been used for cartilage repair in anatomical joints. For a long time, a surgeon wishing to use an implant for cartilage repair could only choose from a selection of ready-made implants, and try to fit these in the best possible way, but over the years, various ways of customizing the implants to the individual patient have been developed, as shown e.g. in WO 2016/005542 and US 2007/0276224.

PROBLEMS WITH THE PRIOR ART

Even though individually customized implants have been used for some time, the positioning of these customized implants has not developed much from the time of the ready-made implants. Even though it is now possible to customize the implant surface, an implant is still generally positioned with its axis tangential to the cartilage surface, as shown e.g. in WO 2016/005542. The advantage of this is that the thickness of the implant usually becomes relatively uniform. However, the positioning of the implant may not be optimal in other respects.

There is a need to address these problems of conventional methods and systems.

SUMMARY

The above described problems are addressed by the claimed system for optimizing a position of an implant having an individually customized implant hat and at least one implant protrusion extending from the implant hat in the direction of an implant axis in an anatomical joint of a patient. The claimed system may comprise a storage media and a processor which is configured to: receive medical image data representing a three dimensional image of the joint from the storage media; obtain a three dimensional virtual model of the joint which is based on the received medical image data; identify damage in the joint based on the received medical image data and/or the three dimensional virtual model of the joint; define an implant area that covers at least a major part of the identified damage; position a virtual implant template having an implant hat corresponding to said implant area in the three dimensional virtual model of the joint; and generate a customized top surface of the implant hat to correspond to a simulated healthy cartilage surface. The processor is configured to position the virtual implant template by: placing the virtual implant template so that the cross section area of the implant hat in a direction perpendicular to the implant axis covers at least a major part of the damage; and optimizing the tilt of the implant axis, while maintaining the position of the cross section area of the implant hat in the joint, by minimizing at least one of: the maximum penetration depth into the bone along the circumference of the implant hat; the total volume of bone and/or cartilage to be removed for implanting the implant; and/or the surface area of the implant penetration into the bone. This makes the implanting less invasive, which is an advantage in many respects, e.g. if the need arises for subsequent implants. Minimizing the maximum penetration depth into the bone along the circumference of the implant hat or minimizing the total volume of bone and/or cartilage to be removed for implanting the implant ensures that the hole to be drilled or reamed in the bone will not become deeper than necessary. The surface area of the implant penetration into the bone may e.g. be determined by multiplying the average depth of the hole to be drilled or reamed in the bone by the circumference.

In embodiments, the processor is configured to position the virtual implant template by placing the virtual implant template so that the implant hat will at all points be thick enough to ensure mechanical stability, and preferably also thick enough to ensure firm anchoring towards cartilage and bone. The processor may e.g. be configured to position the virtual implant template by placing the virtual implant template so that the implant hat at each point of its circumference penetrates at least a predetermined minimum depth into the bone. This ensures that the whole of the implant hat will have at least a minimum thickness, and will thus not easily break.

In embodiments, the processor is configured to restart the optimization of the implant position if at least one predetermined demand on the implant design is not fulfilled. One such predetermined demand on the implant design may be that the implant hat must have a predetermined minimum thickness.

The above described problems are also addressed by the claimed method of optimizing a position of an implant having an individually customized implant hat and at least one implant protrusion extending from the implant hat in the direction of an implant axis in an anatomical joint of a patient. The claimed method may comprise: receiving medical image data representing a three dimensional image of the joint; obtaining a three dimensional virtual model of the joint which is based on the received medical image data; identifying damage in the joint based on the received medical image data and/or the three dimensional virtual model of the joint; defining an implant area that covers at least a major part of the identified damage; positioning a virtual implant template having an implant hat corresponding to said implant area in the three dimensional virtual model of the joint; and generating a customized top surface of the implant hat to correspond to a simulated healthy cartilage surface. The positioning may involve: placing the virtual implant template so that the cross section area of the implant hat in a direction perpendicular to the implant axis covers at least a major part of the damage; and optimizing the tilt of the implant axis, while maintaining the position of the cross section area of the implant hat in the joint, by minimizing at least one of: the maximum penetration depth into the bone along the circumference of the implant hat; the total volume of bone and/or cartilage to be removed for implanting the implant; and/or the surface area of the implant penetration into the bone. This makes the implanting less invasive, which is an advantage in many respects, e.g.

if the need arises for subsequent implants. Minimizing the maximum penetration depth into the bone along the circumference of the implant hat or minimizing the total volume of bone and/or cartilage to be removed for implanting the implant ensures that the hole to be drilled or reamed in the bone will not become deeper than necessary. The surface area of the implant penetration into the bone may e.g. be determined by multiplying the average depth of the hole to be drilled or reamed in the bone by the circumference.

In embodiments, the positioning involves placing the virtual implant template so that the implant hat will at all points be thick enough to ensure mechanical stability, and preferably also thick enough to ensure firm anchoring towards cartilage and bone. The positioning may e.g. involve placing the virtual implant template so that the implant hat at each point of its circumference penetrates at least a predetermined minimum depth into the bone. This ensures that the whole of the implant hat will have at least a minimum thickness, and will thus not easily break.

In embodiments, the optimization of the implant position is restarted if at least one predetermined demand on the implant design is not fulfilled. One such predetermined demand on the implant design may be that the implant hat must have a predetermined minimum thickness.

The implant area may e.g. have the shape of a circle, or two partly overlapping circles, and the implant hat may e.g. have the shape of a cylinder, or two partly overlapping cylinders. The implant area may however have any shape suitable for covering at least a major part of the identified damage, such as e.g. oval or irregular.

The anatomical joint may e.g. be a knee, an ankle, a hip, a toe, an elbow, a shoulder, a finger or a wrist.

The above described problems are also addressed by a non-transitory machine-readable medium on which is stored machine-readable code which, when executed by a processor, controls the processor to perform any one of the above described methods.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Introduction

The present disclosure relates generally to systems and methods for optimizing a position of an implant for cartilage repair in an anatomical joint of a patient. Optimization of implant position may be especially important for implants to be positioned on concave surfaces, such as implants in the knee trochlea groove, since on concave surfaces, the implant angle may be selected in many different ways.

In some embodiments, the anatomical joint is a knee, but the methods and systems presented herein may be used for optimizing the implant position in any suitable anatomical joint, e.g. an ankle, a hip, a toe, an elbow, a shoulder, a finger or a wrist. In a non-limiting example, the implant is intended to be positioned in the trochlea area of an anatomical joint.

The medical image data may be retrieved directly from a digital imaging and communications in medicine (DICOM) file or any other suitable image file format. The DICOM format, or a comparable image file format, is advantageous for visualizing different parts of the anatomical joint. The DICOM format, or a comparable image file format, may be used for visualizing different parts of a knee, such as the femoral condyles and the trochlea area, or different parts of any other relevant anatomical joint that is being investigated, such as the talus of the ankle.

The three dimensional virtual model of the joint may be obtained in many different ways. It may e.g. be obtained from a storage media, or be generated based on a series of radiology images captured during a process of scanning radiology images through different layers of the anatomical joint or part of it, which captures all the radiology image data necessary to generate a three dimensional virtual model of the anatomical joint or part of it in an image segmentation process based on said radiology images. The three dimensional virtual model may be used for visualizing tissues, bone, cartilage and damages in relation to femoral knee bone and cartilage, or bone and cartilage of any other relevant anatomical joint that is being investigated.

The processor may in some embodiments comprise several different processors which together perform the claimed functions. In the same way, the storage media may in some embodiments comprise several different storage media which together perform the claimed functions.

The implant axis is the axis of the at least one implant protrusion, which fixates the implant. The implant protrusion may e.g. be an implant peg or a screw. For a circular implant, the implant axis normally runs through the center of, and perpendicular to, the circular implant hat.

System and method embodiments of the disclosed solution are presented in more detail in connection with the figures.

System Architecture

Figure 1:
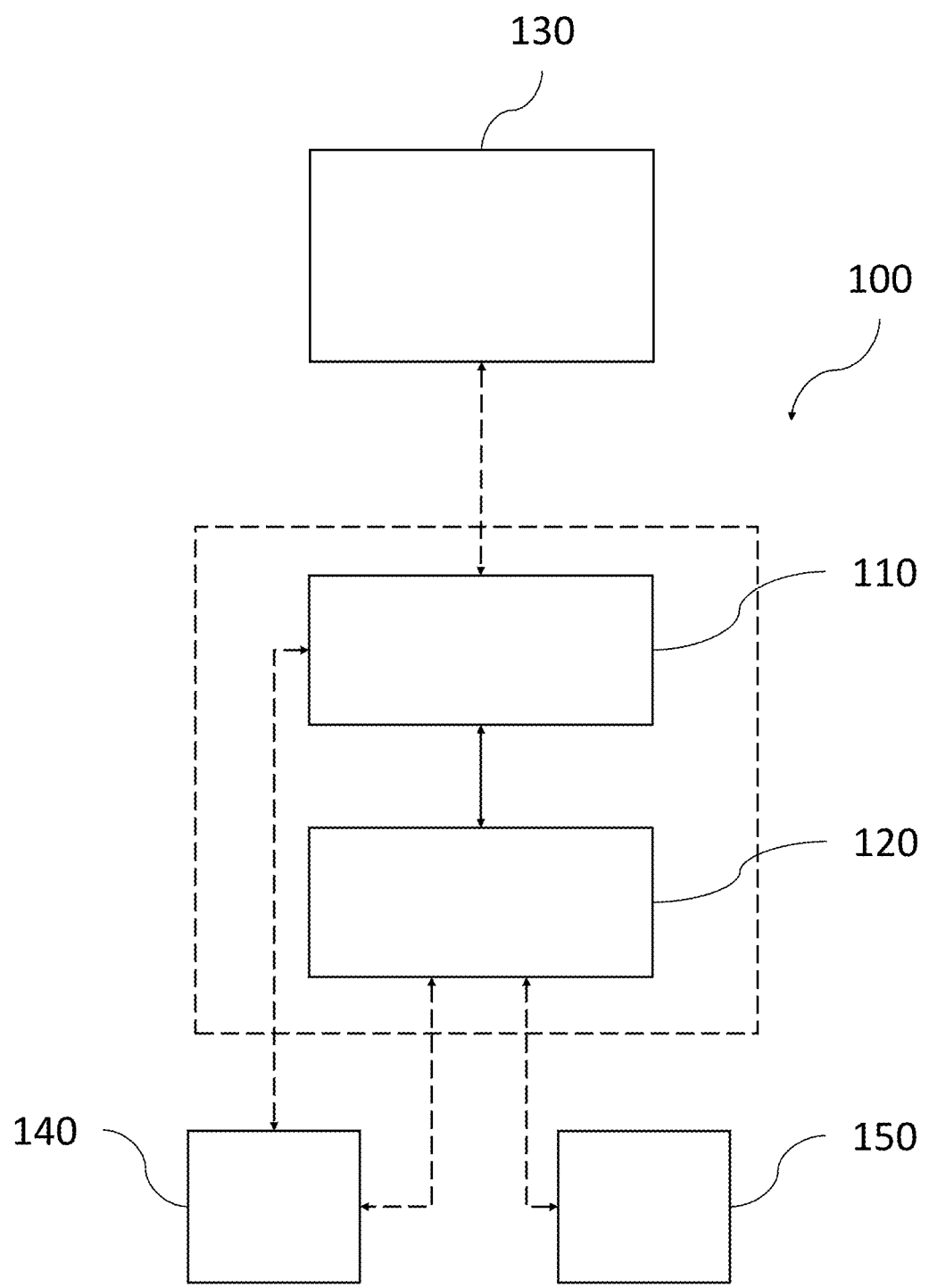
FIG. 1 shows a schematic view of a system for optimizing an implant position in an anatomical joint of a patient, in accordance with one or more embodiments described herein.

FIG. 1 shows a schematic view of a system 100 for optimizing a position of an implant having an individually customized implant hat H and at least one implant protrusion in the form of an implant peg P extending from the implant hat H in the direction of an implant axis A in an anatomical joint of a patient. According to embodiments, the system 100 comprises a storage media 110, configured to receive and store image data and parameters. In some embodiments, the system 100 is communicatively coupled, as indicated by the dashed arrow in FIG. 1, to an imaging system 130. The imaging system 130 may be configured to capture or generate radiology images, such as for example X-ray images, ultrasound images, computed tomography (CT) images, nuclear medicine including positron emission tomography (PET) images, and magnetic resonance imaging (MRI) images. The storage media 110 may be configured to receive and store medical image data from the imaging system 130.

According to embodiments, the system 100 further comprises a processor 120, which may for example be a general data processor, or other circuit or integrated circuit capable of executing instructions to perform various processing operations.

In one or more embodiments, the processor 120 is configured to:

receive medical image data representing a three dimensional image of the joint from the storage media 110;

obtain a three dimensional virtual model of the joint which is based on the received medical image data;

identify damage in the joint based on the received medical image data and/or the three dimensional virtual model of the joint;

defining an implant area that covers at least a major part of the identified damage;

position a virtual implant template having an implant hat corresponding to said implant area in the three dimensional virtual model of the joint; and generate a customized top surface of the implant hat H to correspond to a simulated healthy cartilage surface, wherein the processor 120 is configured to position the virtual implant template by:

placing the virtual implant template so that the cross section area of the implant hat H in a direction perpendicular to the implant axis A covers at least a major part of the damage; and optimizing the tilt of the implant axis A, while maintaining the position of the cross section area of the implant hat H in the joint, by minimizing at least one of:

the maximum penetration depth $D_{max}$ into the bone along the circumference of the implant hat H;

the total volume of bone and/or cartilage to be removed for implanting the implant; and/or the surface area of the implant penetration into the bone.

The medical image data may for example be captured during a process of scanning radiology images through different layers of the anatomical joint or part of it, which captures all the radiology image data necessary to generate a three-dimensional virtual model of the anatomical joint or part of it in an image segmentation process based on the medical image data.

The damage may be identified automatically by the processor 120, or be identified manually by an operator of the system with the help of the processor 120. In some embodiments, damage may be identified for both bone parts and cartilage parts of the anatomical joint. Alternatively, damage to bone parts only, or damage to cartilage parts only, or damage to other tissue parts such as tendons or ligaments, may be identified, depending on the application.

The implant area may have the shape of a circle, or two partly overlapping circles, but the implant area may have any shape suitable for covering at least a major part of the identified damage, such as e.g. oval or irregular.

The implant area may be defined automatically by the processor 120, or manually by an operator of the system with the help of the processor 120. In embodiments, the processor 120 may be configured to select a suitable implant shape from a predefined set of implant shapes, for an implant area in the shape of a circle or two partly overlapping circles e.g. with varying diameters for the one or two circles. In this context, a suitable implant shape means an implant shape having a type and dimensions that match the identified damage, thereby making it a suitable shape for an implant for repairing the identified damage. In embodiments, the processor 120 is configured to determine the diameter of one or two circles so that an implant area in the shape of a circle or two partly overlapping circles covers at least a major part of the identified damage. For an implant in the shape of two partly overlapping circles, a so called twin implant, the two circles of the twin circle preferably have the same diameter, so that the same drill and the same drill guide can be used to drill both holes. The overlap between the two circles of the twin circle is preferably fixed, but may also be adjustable to the shape of the damage.

If the implant area has the shape of a circle, the implant hat preferably has the shape of a cylinder. If the implant area has the shape of two partly overlapping circles, the implant hat preferably has the shape of two partly overlapping cylinders. The implant hat may thus have any shape that corresponds to the implant area.

The virtual implant template may be positioned in the three dimensional virtual model of the joint automatically by the processor 120, or be positioned in the three dimensional virtual model of the joint manually by an operator of the system with the help of the processor 120. In embodiments, the processor 120 proposes alternative positions from which the operator of the system can choose. It may also be possible for the operator of the system to manually adjust an automatically generated virtual implant template position.

The processor 120 does not necessarily position the virtual implant template to cover all the identified damage—as long as a major part of the damage is covered, the implant may still be used for cartilage repair. It is sometimes not desirable to use an implant which is large enough to cover all the identified damage, since this may lead to the unnecessary removal of healthy bone and/or cartilage when the identified damage does not have the same shape as the implant.

The processor 120 may be configured to position the virtual implant template by placing the virtual implant template so that the implant hat H will at all points be thick enough to ensure mechanical stability, and preferably also thick enough to ensure firm anchoring towards cartilage and bone. If the hat H of the implant is too thin in certain points, the risk of it breaking may be too high. Further, if the hat H of the implant is not thick enough to ensure firm anchoring towards cartilage and bone, there may be a risk of liquid penetrating the surface under the hat H, so that the implant may be loosened. The mechanical stability and/or the firm anchoring may e.g. be ensured by the processor being configured to place the virtual implant template so that the implant hat H at each point of its circumference penetrates at least a predetermined minimum depth $D_{min}$ into the bone. $D_{min}$ may be any suitable depth, such as e.g. 2 or 3 mm. $D_{min}$ may also be 0 mm, if it is enough that the implant hat H at least touches the bone along its whole circumference. Since the cartilage has a certain thickness, it may be enough to ensure that the implant hat H at least touches the bone along its whole circumference in order to ensure that the implant hat H has at least a minimum thickness at all points.

The processor 120 may optimize the tilt of the implant axis A in many different ways.

The processor 120 may optimize the tilt of the implant axis A by minimizing the maximum penetration depth $D_{max}$ into the bone along the circumference of the implant hat H. This ensures that the hole to be drilled or reamed in the bone will not become deeper than necessary.

The processor 120 may optimize the tilt of the implant axis A by minimizing the total volume of bone and/or cartilage to be removed for implanting the implant. This optimization is especially advantageous when implanting a twin implant, which may have more than one protrusion, or when implanting an implant in a concave surface of a joint. Even if the implant in some points penetrates deep into the bone, the total volume to be drilled or reamed away may be smaller if the tilt of the implant axis A is optimized by minimizing the total volume of bone and/or cartilage to be removed for implanting the implant.

The processor 120 may optimize the tilt of the implant axis A by minimizing the surface area of the implant penetration into the bone. The surface area may e.g. be determined by multiplying the average depth of the hole to be drilled or reamed in the bone by the circumference.

In embodiments, the processor 120 is configured to restart the optimization of the implant position if at least one predetermined demand on the implant design is not fulfilled. One such predetermined demand on the implant design may be that the implant hat H must have a predetermined minimum thickness $T_{min}$.

In one or more embodiments, the system 100 may optionally comprise a display 140 configured to display image data. The display 140 may be configured to receive image data for display via the processor 120, and/or to retrieve image data for display directly from the storage media 110, possibly in response to a control signal received from the processor 120 or an inputter 150, which is further presented below. The processor 120 may be configured to visualize the identified damage in the three dimensional virtual model of the joint using the display 140.

In some embodiments, the system 100 may further optionally comprise one or more inputters 150 configured to receive user input. The inputter 150 is typically configured to interpret received user input and to generate control signals in response to said received user input. The display 140 and the inputter 150 may be integrated in, connected to or communicatively coupled to the system 100. The inputter 150 may for instance be configured to interpret received user input that is being input in connection with a displayed virtual model, and generate control signals in response to said received user input, to trigger display of an image or manipulation of image data being displayed, wherein the manipulations may be temporary or permanent. Such manipulations may for example include providing annotations, moving or changing an image or part of an image, changing the viewing perspective, zooming in or out, and/or any other suitable form of manipulation that enables the user to view and analyze the displayed image data in an improved manner. An inputter 150 may for example comprise a selection of a keyboard, a computer mouse, one or more buttons, touch functionality, a joystick, and/or any other suitable input device. In some embodiments, the processor 120 may be configured to receive a control signal from the inputter 150 and to process image data that is being displayed using display 140, or in other words manipulate a displayed image, in response to the received control signal.

In some embodiments, the anatomical joint is a knee. In other embodiments, the anatomical joint may be any other anatomical joint suitable for damage determination using image data analysis, such as an ankle, a hip, a toe, an elbow, a shoulder, a finger or a wrist.

The processor 120 may be configured to perform the method steps of any or all of the embodiments presented herein.

Method Embodiments

Figure 2:
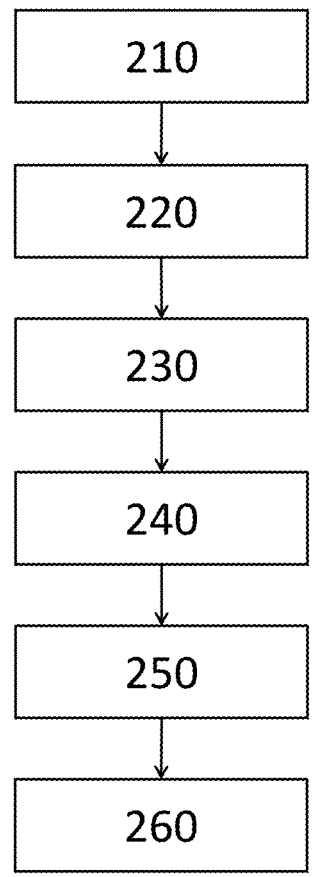
FIG. 2 is a flow diagram for a method for optimizing an implant position in an anatomical joint, in accordance with one or more embodiments described herein.

FIG. 2 is a flow diagram for a method 200 for optimizing a position of an implant having an individually customized implant hat H and at least one implant protrusion P extending from the implant hat H in the direction of an implant axis A in an anatomical joint. In accordance with one or more to embodiments, the method 200 comprises:

In step 210: receiving medical image data representing a three dimensional image of the joint.

The medical image data may for example be captured during a process of scanning radiology images through different layers of the anatomical joint or part of it, which captures all the radiology image data necessary to generate a three-dimensional virtual model of the anatomical joint or part of it in an image segmentation process based on the medical image data.

In some embodiments, the anatomical joint is a knee. In other embodiments, the anatomical joint may be any other anatomical joint suitable for damage determination using image data analysis, such as an ankle, a hip, a toe, an elbow, a shoulder, a finger or a wrist.

In step 220: obtaining a three dimensional virtual model of the joint which is based on the received medical image data.

In step 230: identifying damage in the joint based on the received medical image data and/or the three dimensional virtual model of the joint.

The damage may be identified automatically or manually. In some embodiments, damage may be identified for both bone parts and cartilage parts of the anatomical joint. Alternatively, damage to bone parts only, or damage to cartilage parts only, or damage to other tissue parts, may be identified, depending on the application. It may in some embodiments be advantageous to analyze both bone and cartilage of the depicted joint in the input medical image data, as the combination of the two may provide additional information, but all embodiments described herein may also be performed when only one of the substances bone and cartilage, or any other tissue part, of the depicted joint is analyzed.

In one or more embodiments, method step 230 comprises detecting that the intensity in an area within or adjacent to the bone and/or cartilage parts of the anatomical joint is higher or lower than a predetermined threshold. Depending on the settings of the imaging device that has captured the analyzed medical image data, the analyzed image may for example represent the following substances with different intensity levels: cortical bone, liquids, cartilage, fat/bone marrow and meniscus. Different intensity levels in the analyzed image correspond to different signal intensity levels and these may typically be represented by pixel/voxel values ranging from 0 to 1, or in a visual representation shown as grey scale levels from white to black. In embodiments where the pixel/voxel values range from 0 to 1, a predetermined threshold is set to a suitable value between 0 and 1, or in other words to a suitable grey scale value.

In one or more embodiments, method step 230 further, or alternatively, comprises detecting an irregular shape of a contour of the at least one tissue part of the anatomical joint and determining whether this represents a damage to the anatomical joint.

In one or more embodiments, method step 230 comprises marking, visualizing or in another way indicating the identified damage to the anatomical joint. Marking, visualizing, or indicating the identified damage may include changing the pixel/voxel value of one or more pixels/voxels on, in connection with, or surrounding a pixel/voxel identified to belong to identified damage, such that the identified damage is visually distinguished and noticeable to a user/viewer. Such a change of pixel/voxel values of one or more pixels/voxels on, in connection with, or surrounding a pixel/voxel identified to belong to identified damage may for example comprise a selection of the following:

changing the luminance/intensity values of one or more pixels/voxels identified as being located on identified damage;
changing one or more chrominance/color values of one or more pixels/voxels identified as being located on identified damage;
changing the luminance/intensity values of one or more pixels/voxels identified as surrounding identified damage;
changing one or more chrominance/color values of one or more pixels/voxels identified as surrounding identified damage; and/or
adding an annotation, symbol or other damage indicator to the image, in connection with one or more pixels/voxels identified as being located on, or surrounding, identified damage.

In step 240: defining an implant area that covers at least a major part of the identified damage.

The implant area may e.g. have the shape of a circle, or two partly overlapping circles, and the implant hat may e.g. have the shape of a cylinder, or two partly overlapping cylinders. The implant area may however have any shape suitable for covering at least a major part of the identified damage, such as e.g. oval or irregular.

The implant area may be defined automatically or manually. In embodiments, a suitable implant shape may be selected from a predefined set of implant shapes, for an implant area in the shape of a circle or two partly overlapping circles e.g. with varying diameters for the one or two circles. In this context, a suitable implant shape means an implant shape having a type and dimensions that match identified damage, thereby making it a suitable shape for an implant for repairing the identified damage. In embodiments, the diameter or diameters of one or two circles is determined so that an implant area in the shape of a circle or two partly overlapping circles covers at least a major part of the identified damage. For an implant in the shape of two partly overlapping circles, a twin implant, the two circles of the twin circle preferably have the same diameter, so that the same drill and the same drill guide can be used to drill both holes. The overlap between the two circles of the twin circle is preferably fixed, but may also be adjustable to the shape of the damage.

In step 250: positioning a virtual implant template in the three dimensional virtual model of the joint.

The virtual implant template may be positioned automatically or manually. It may also be possible for the operator of the system to manually adjust an automatically generated virtual implant template position.

In different embodiments, the positioning in step 250 may involve:
placing the virtual implant template so that at least a major part of the damage is covered; and
optimizing the tilt of the implant axis A, while maintaining the position of the cross section area of the implant hat H in a direction perpendicular to the implant axis A in the joint, by minimizing at least one of:
the maximum penetration depth $D_{max}$ into the bone along the circumference of the implant hat H;
the total volume of bone and/or cartilage to be removed for implanting the implant; and/or
the surface area of the implant penetration into the bone.

The virtual implant template does not have to cover all the identified damage—as long as a major part of the damage is covered, the implant may still be used for cartilage repair. It is sometimes not desirable to use an implant which is large enough to cover all the identified damage, since this may lead to the unnecessary removal of healthy bone and cartilage when the identified damage does not have the same shape as the implant.

The positioning may involve placing the virtual implant template so that the implant hat H will at all points be thick enough to ensure mechanical stability, and preferably also thick enough to ensure firm anchoring towards cartilage and bone. If the hat H of the implant is too thin in certain points, the risk of it breaking may be too high. Further, if the hat H of the implant is not thick enough to ensure firm anchoring towards cartilage and bone, there may be a risk of liquid penetrating the surface under the hat H, so that the implant may be loosened. The mechanical stability and/or the firm anchoring may e.g. be ensured by the positioning involving placing the virtual implant template so that the implant hat H at each point of its circumference penetrates at least a predetermined minimum depth $D_{min}$ into the bone. $D_{min}$ may be any suitable depth, such as e.g. 2 or 3 mm. $D_{min}$ may also be 0 mm, if it is enough that the implant hat H at least touches the bone along its whole circumference. Since the cartilage has a certain thickness, it may be enough to ensure that the implant hat H at least touches the bone along its whole circumference in order to ensure that the implant hat H has at least a minimum thickness at all points.

The tilt of the implant axis A may be optimized in many different ways.

The tilt of the implant axis A may e.g. be optimized by minimizing the maximum penetration depth $D_{max}$ into the bone along the circumference of the implant hat H. This ensures that the hole to be drilled or reamed in the bone will not become deeper than necessary.

The tilt of the implant axis A may e.g. be optimized by minimizing the total volume of bone and/or cartilage to be removed for implanting the implant. This optimization is especially advantageous when implanting a twin implant having more than one protrusion, or when implanting an implant in a concave surface of a joint. Even if the implant in some points penetrates deep into the bone, the total volume to be drilled or reamed away may be smaller if the tilt of the implant axis A is optimized by minimizing the total volume of bone and/or cartilage to be removed for implanting the implant.

The tilt of the implant axis A may e.g. be optimized by minimizing the surface area of the implant penetration into the bone. The surface area may e.g. be determined by multiplying the average depth of the hole to be drilled or reamed in the bone by the circumference.

Figure 3:
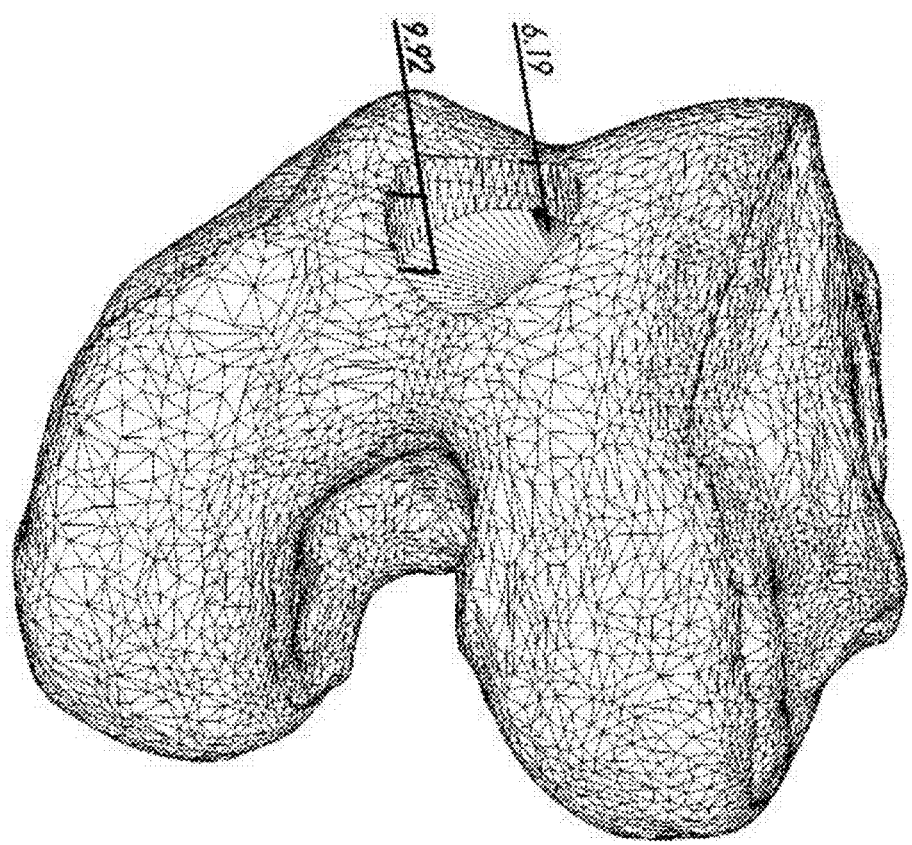
FIG. 3 shows an image of a three dimensional virtual model of a part of a joint where the maximum and minimum penetration depths of an implant at a selected axis tilt have been indicated.

When the tilt of the implant axis A is optimized, the penetration into the bone may be visualized. FIG. 3 shows an image of a three dimensional virtual model of a part of a joint where the maximum and minimum penetration depths of a circular implant at a selected axis tilt have been indicated. This visualization makes it easier to manually optimize the tilt of the implant axis A. When the tilt of the implant axis A is optimized automatically, the visualization is not necessary, but may be used to double-check the automated procedure.

Figure 4:
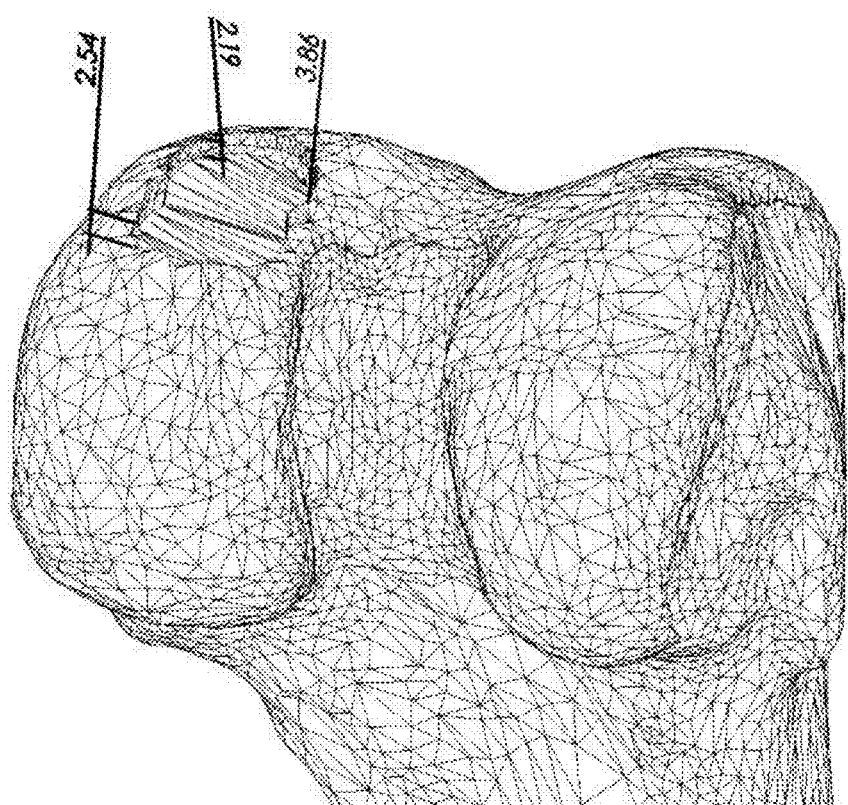
FIG. 4 shows an image of a three dimensional virtual model of a part of a joint where the maximum and minimum penetration depths of an implant with two axes at selected axis tilts have been indicated.

For an asymmetric implant such as e.g. a twin implant, the optimization may be slightly more complicated, since the implant can be rotated in different ways. Before the optimization of the tilt of the implant axis A for the twin implant, the rotation around the axis A should preferably be defined, since a twin implant is not symmetric around the implant axis A, as a circular implant. FIG. 4 shows an image of a three dimensional virtual model of a part of a joint where the maximum and minimum penetration depths for the twin circle of a twin implant have been indicated. This visualization makes it easier to manually optimize the tilt of the implant axis. When the tilt of the implant axis is optimized automatically, the visualization is not necessary, but may be used to double-check the automated procedure.

Figure 5A:
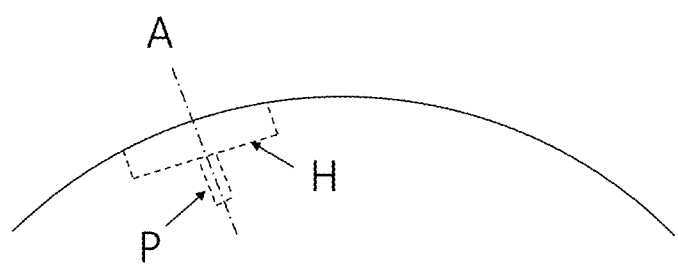
FIGS. 5a and 5b show schematic examples of different potential implant positions in an anatomical joint, in accordance with one or more embodiments described herein.
Figure 5B:
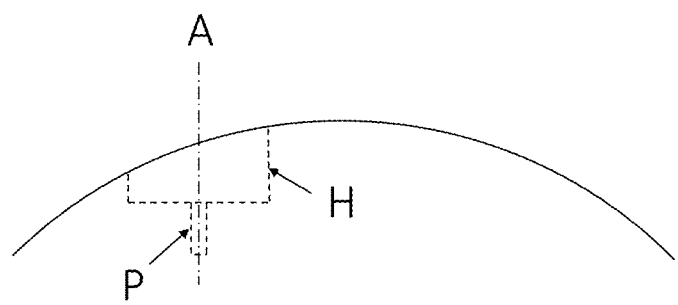

FIGS. 5a and 5b show schematic examples of different potential implant positions in an anatomical joint, in accordance with one or more embodiments described herein. More specifically, FIG. 5a shows an implant with a circular implant hat H and an implant protrusion in the form of an implant peg P, positioned so that the implant axis A is substantially parallel to the surface normal at the center of the implant, while FIG. 5b shows an implant positioned in a different way. The positioning according to FIG. 5a may minimize the average penetration depth or the maximum penetration depth, but may not minimize the total volume of bone and/or cartilage to be removed for implanting the implant or the surface area of the implant penetration into the bone.

Figure 6A:
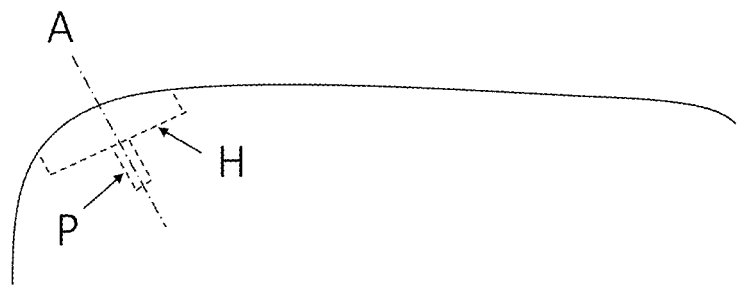
FIGS. 6a and 6b show other schematic examples of different potential implant positions in an anatomical joint, in accordance with one or more embodiments described herein.
Figure 6B:
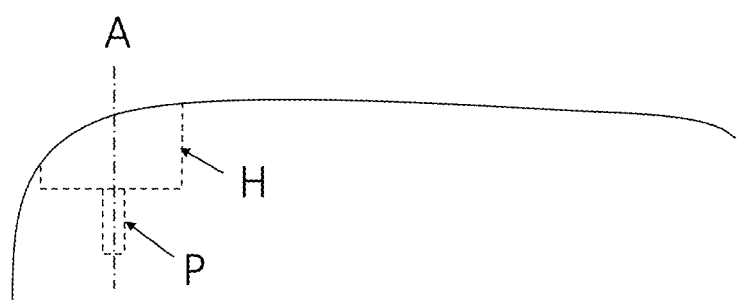

FIGS. 6a and 6b show other schematic examples of different potential implant positions in an anatomical joint, in accordance with one or more embodiments described herein. More specifically, FIG. 6a shows an implant with a circular implant hat H and an implant protrusion in the form of an implant peg P, positioned so that the implant axis A is substantially parallel to the surface normal at the center of the implant, while FIG. 6b shows an implant positioned in a different way. The positioning according to FIG. 6a may minimize the average penetration depth or the maximum penetration depth, but may not minimize the total volume of bone and/or cartilage to be removed for implanting the implant or the surface area of the implant penetration into the bone.

Figure 7A:
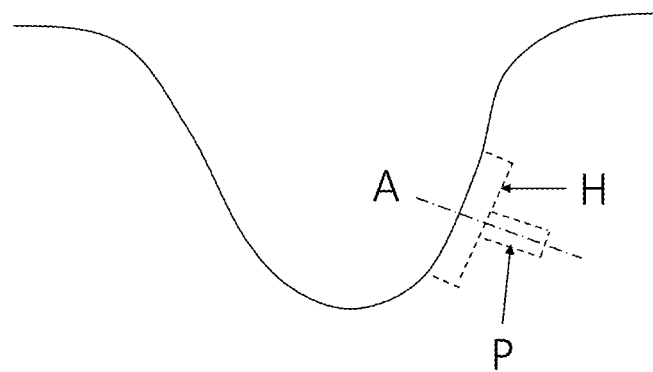
FIGS. 7a and 7b show yet other schematic examples of different potential implant positions in an anatomical joint, in accordance with one or more embodiments described herein.
Figure 7B:
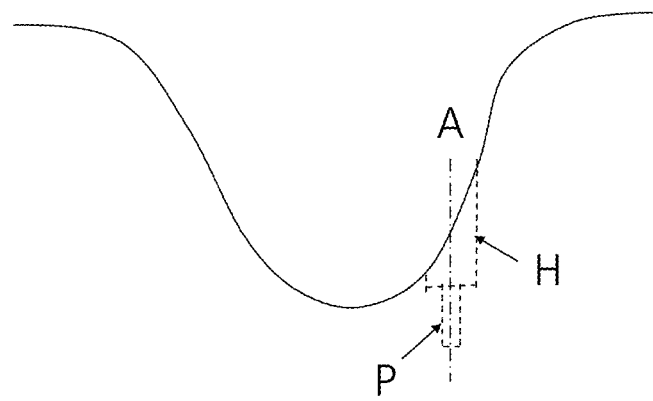

FIGS. 7a and 7b show yet other schematic examples of different potential implant positions in an anatomical joint, in accordance with one or more embodiments described herein. More specifically, FIG. 7a shows an implant with a circular implant hat H and an implant protrusion in the form of an implant peg P, positioned so that the implant axis A is substantially parallel to the surface normal at the center of the implant, while FIG. 7b shows an implant positioned in a different way. When the implant is to be positioned in a joint having the shape shown in FIGS. 7a and 7b, the implant position may be more optimized if the total volume of bone and/or cartilage to be removed for implanting the implant or the surface area of the implant penetration into the bone is minimized than if the maximum penetration depth $D_{max}$ into the bone along the circumference of the circular implant hat H is minimized.

Figure 8A:
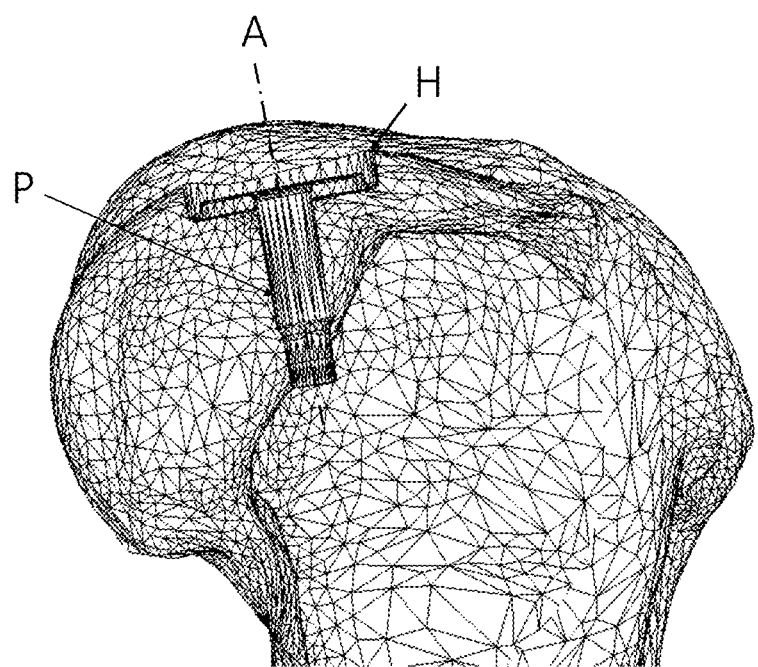
FIGS. 8a and 8b show examples of different potential implant positions in an anatomical joint, in accordance with one or more embodiments described herein.
Figure 8B:
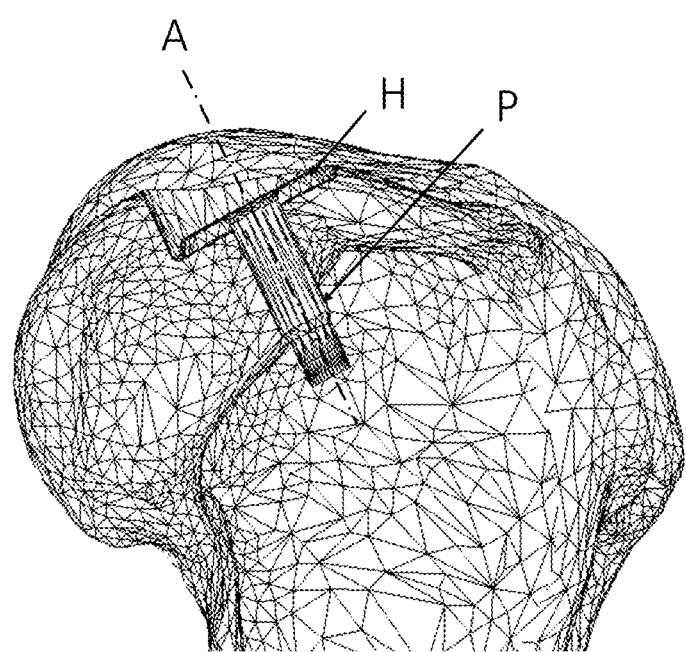

FIGS. 8a and 8b show examples of different potential implant positions in an anatomical joint, in accordance with one or more embodiments described herein. More specifically, FIG. 8a shows a virtual implant with a circular implant hat H and an implant protrusion in the form of an implant peg P, positioned so that the implant axis A is almost parallel to the surface normal at the center of the implant, while FIG. 8b shows a virtual implant positioned in a different way. The positioning according to FIG. 8a may minimize the average penetration depth or the maximum penetration depth, but may not minimize the total volume of bone and/or cartilage to be removed for implanting the implant or the surface area of the implant penetration into the bone.

The customized top surface of the implant hat H may be generated to correspond to a simulated healthy cartilage surface. The customized top surface of the implant hat H may e.g. be simulated based on the curvature of the cartilage immediately surrounding the area of damaged cartilage. A suitable area comprising and extending around the damaged cartilage may be selected, and the curvature of the whole area simulated in such a way that the curvature of the area which is not damaged matches the simulated curvature. A simulated healthy surface of the area of damaged cartilage may thereby be generated. The simulation may comprise an interpolation, e.g. using the Solid Works Surface Wizard or another suitable tool.

Figure 9A:
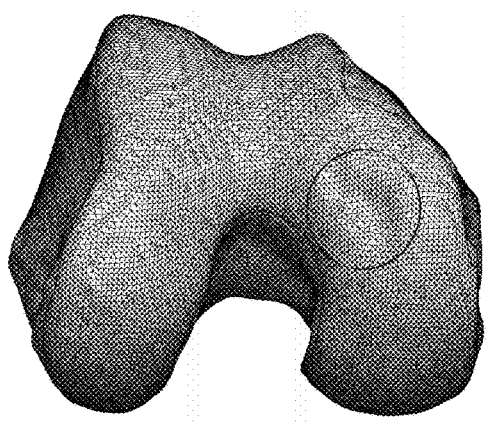
FIGS. 9a-d show the design of an implant having a surface which corresponds to a simulated healthy cartilage surface in a three dimensional virtual model of an anatomical joint.
Figure 10A:
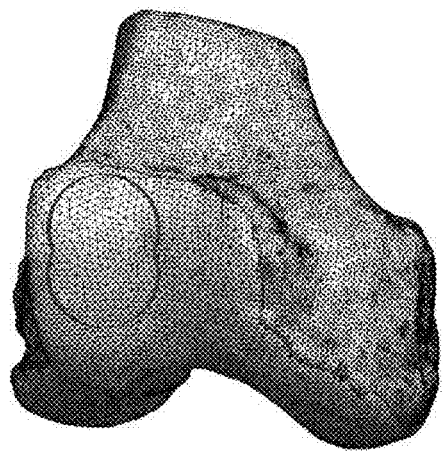
FIGS. 10a-d show the design of an implant with a surface shape corresponding to two partly overlapping circles having a surface which corresponds to a simulated healthy cartilage surface in a three dimensional virtual model of an anatomical joint.

FIGS. 9a and 10a show an image of a three dimensional virtual model in the form of a 3D mesh model of the cartilage and femoral bone of a knee. The 3D mesh model may be generated based on any suitable imaging methods, such as e.g. MRI. In the image of the 3D mesh model, the implant position has been marked with a circle in FIG. 9a, and two partly overlapping circles, a twin circle, in FIG. 10a. The circle, or twin circle, corresponds to the circumferential shape of the implant hat H. At least parts of the surface within this circle or twin circle comprises damaged cartilage, and possibly also damaged subchondral bone beneath the cartilage. The size and shape of the implant hat H is preferably selected based on the extent of damage, so that at least most of the damaged area is removed and replaced by the implant. Sometimes all of the surface within the circle or circles will be damaged, and some of the damaged area will not be removed, and sometimes the volume to be removed will comprise also some healthy cartilage and/or subchondral bone.

Figure 9B:
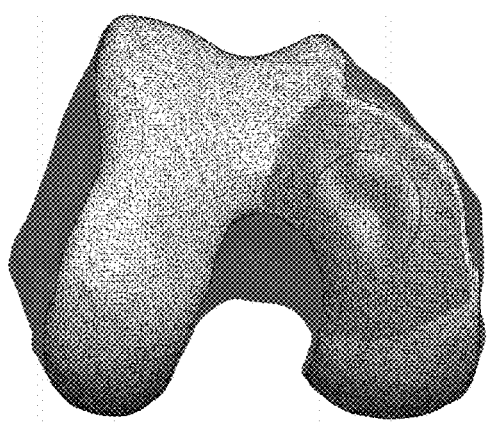
Figure 10B:
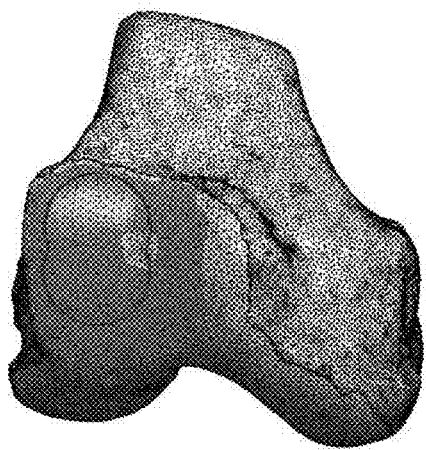

FIGS. 9b and 10b show the selection of a suitable area for simulating the curvature of the surface. The area is preferably large enough to have sufficient curvature in all directions surrounding the area of damaged cartilage, without containing any sharp edges which could distort the simulation. The area may e.g. be selected based on the distance from the damaged cartilage and the curvature, e.g. so that the whole area within a predetermined distance from the damaged cartilage is selected provided that the curvature within this area is below a certain threshold. Sections falling within a predetermined distance from the damaged cartilage but exceeding the curvature threshold would then be excluded from the area.

Figure 9C:
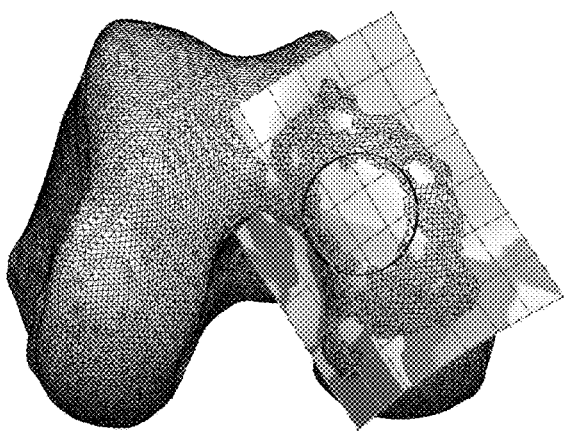
Figure 10C:
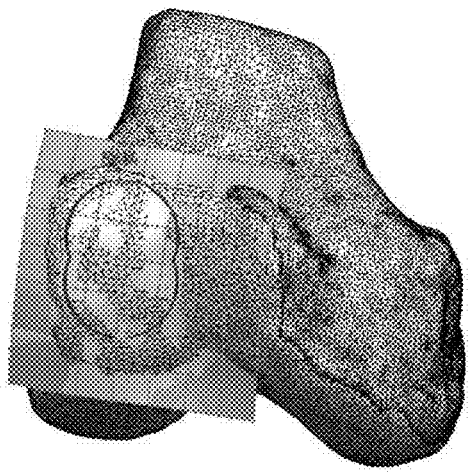

FIGS. 9c and 10c show a simulation of the curvature of the whole area, including a tangent interpolation over the area of damaged cartilage. The generated surface is defined by curvature lines along the length and the width, points along which curvature lines coincide with the points of the 3D mesh model in the areas of healthy cartilage. Only healthy cartilage surfaces are preferably used as a basis for this tangent interpolation; all potentially damaged areas are preferably excluded. In FIGS. 9c and 10c, the healthy mesh areas shown with triangles within the surface generating grid are used as a basis for the tangent interpolation, and the blank areas are excluded. Preferably, all areas of damaged cartilage are excluded from being the basis of the interpolation. After the interpolation, the deviation between the interpolated area and the actual area within the areas of healthy cartilage may be analyzed in order to ascertain that the interpolated area does not differ too much from the actual area in the areas of healthy cartilage. If there is too much deviation, a new interpolation may be necessary.

Figure 9D:
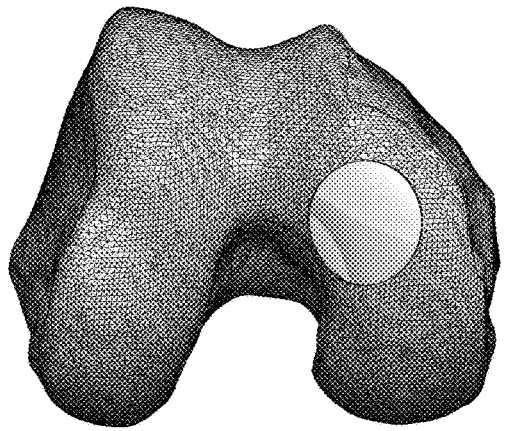
Figure 10D:
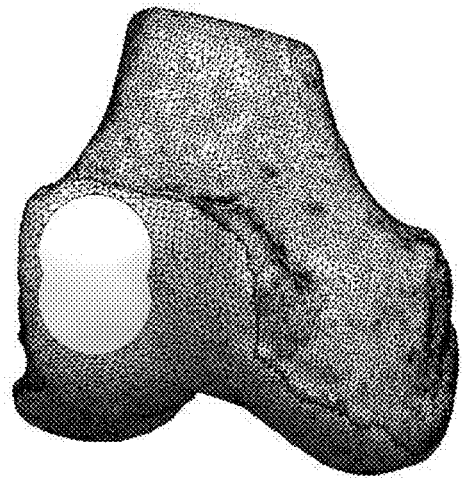

When the healthy cartilage surface has been simulated, the area is trimmed to match the defined implant shape, as shown in FIGS. 9d and 10d. A 3D mesh model of the cartilage and bone of the knee comprising the implant may then be generated, so that it can be determined that the knee with the implant matches the surrounding surfaces. This evaluation may e.g. be done layer by layer in MRI software.

Use Case Embodiment

To set the presently disclosed methods and systems in a larger context, the method of optimizing an implant position in an anatomical joint of a patient according to any of the disclosed embodiments may in use case embodiments be preceded by capturing and/or obtaining medical image data representing an anatomical joint, and may further be followed by the design and production of a medical implant.

Figure 11:
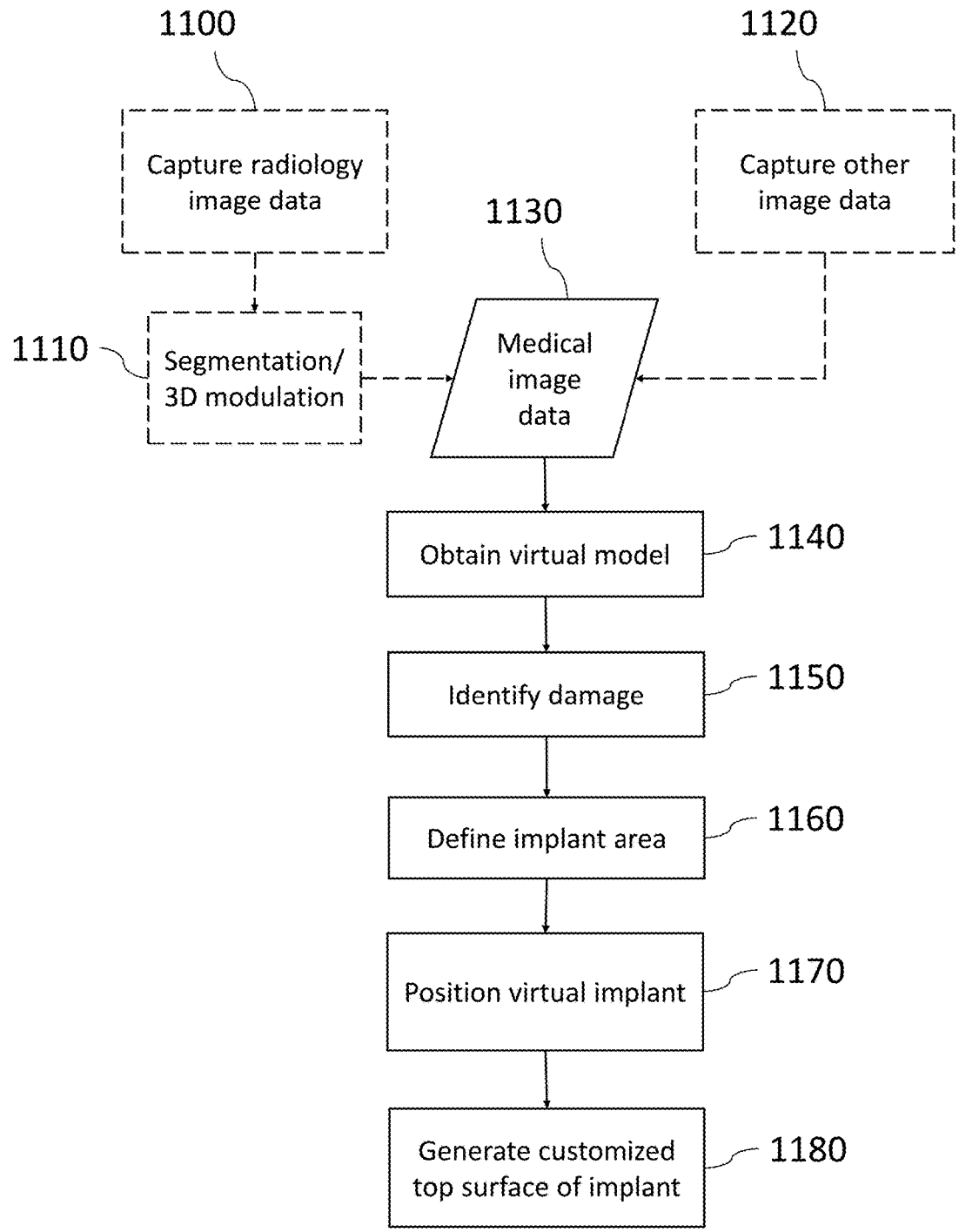
FIG. 11 shows a flow diagram exemplifying the steps from the capturing of radiology image data to the design and production of a medical implant, in accordance with one or more embodiments described herein.

FIG. 11 is a flow diagram exemplifying one such larger context, including receiving radiology/medical image data from an image source, obtaining a three dimensional virtual model of the joint, identifying damage in the joint, defining an implant area based on the identified damage, and positioning a virtual implant template in the virtual model, in accordance with one or more embodiments described herein. In FIG. 11, the various ways of generating the medical image data is marked with dashed lines to clarify that they are optional steps shown in the figure to provide context only, and not essential to any of the embodiments presented herein.

According to the example shown in FIG. 11, medical image data may be obtained in a step 1100 in the form of radiology image data from a radiology imaging system. The radiology image data obtained may for example be generated using one or more of a variety of imaging techniques such as X-ray images, ultrasound images, computed tomography (CT) images, nuclear medicine including positron emission tomography (PET) images, and magnetic resonance imaging (MRI) images. The radiology image data may for example be captured during a process of scanning radiology images through different layers of the anatomical joint or part of it, which captures all the radiology image data necessary to generate a three dimensional virtual model of the anatomical joint or part of it based on the radiology image data.

The image data obtained in step 1100 may further be processed in a step 1110, by performing segmentation and 3D modulation to obtain a three dimensional virtual model of what is depicted in the captured image data. For instance, if the image data captured depict an anatomical joint, the three dimensional virtual model would be a three dimensional virtual model of the anatomical joint. Medical image data may also be obtained in step 1120 from a different kind of image source that provides 2D image data. The three dimensional virtual model and the 2D image data both depict the same object, namely the anatomical joint of interest for damage determination. The 2D image data and the three dimensional virtual model may represent only a part of the anatomical joint.

In a use case embodiment, an operator may use the system as follows. The operator receives 1130 medical image data representing a three dimensional image of the joint, and obtains 1140 a three dimensional virtual model of the joint based on the received medical image data. The three dimensional virtual model may be generated by the system or retrieved from another source. Damage in the joint is then identified 1150 based on the received medical image data and/or the three dimensional virtual model of the joint, either automatically by the system or manually by the operator. Damage in the joint may be identified based on the received medical image data before the three dimensional virtual model of the joint is obtained.

The operator then defines 1160 an implant area that covers at least a major part of the identified damage. If the identified damage has a shape making it unsuitable for repair with a circular implant, a twin implant may be used instead, and in that case, the area will have the shape of two partly overlapping circles, a twin circle. The implant area may however have any shape suitable for covering at least a major part of the identified damage, such as e.g. oval or irregular.

The area may be defined automatically by the processor 120, manually by the operator with the help of the processor 120, or entirely manually by the operator. A suitable implant shape may e.g. be selected from a predefined set of implant shapes, for an implant area in the shape of a circle or two partly overlapping circles e.g. with varying diameters for the one or two circles. In this context, a suitable implant shape means an implant shape having a type and dimensions that match the identified damage, thereby making it a suitable shape for an implant for repairing the identified damage. The area should have a size and shape essentially corresponding to the size of the identified damage, but may be slightly larger or slightly smaller. If the identified damage has a shape making it unsuitable for repair with a circular implant, a twin implant may e.g. be used instead. In embodiments, the diameter or diameters of one or two circles is determined so that an implant area in the shape of a circle or two partly overlapping circles covers at least a major part of the identified damage. For an implant in the shape of two partly overlapping circles, a twin implant, the two circles of the twin circle preferably have the same diameter, so that the same drill and the same drill guide can be used to drill both holes. The overlap between the two circles of the twin circle is preferably fixed, but may also be adjustable to the shape of the damage.

The operator then positions 1170 a virtual implant template in the three dimensional virtual model of the joint. The virtual implant template may preferably have an implant hat H corresponding to the implant area. In the case of a circular implant, the implant hat H preferably has the shape of a cylinder. In the case of a twin implant, the implant hat H instead preferably has the shape of two partly overlapping cylinders. The positioning may be automated or manual, or partly automated and partly manual, e.g. by the processor 120 proposing a position which can then be adjusted manually by the operator. The system may e.g. automatically propose a position which the operator can then adjust manually. The virtual implant template is first placed so that the cross section area of the implant hat H in a direction perpendicular to the implant axis A covers at least a major part of the damage. Then, the implant axis A is tilted, while the position of the cross section area of the implant hat H in the joint is maintained. The tilt of the implant axis A is optimized by minimizing at least one of: the maximum penetration depth $D_{max}$ into the bone along the circumference of the implant hat H; the total volume of bone and/or cartilage to be removed for implanting the implant; and/or the surface area of the implant penetration into the bone.

During the positioning, the maximum and minimum penetration depths of the implant at selected axis tilts may be visualized, as shown in FIGS. 3 and 4. If the operator positions the selected implant template manually or partly manually, such a visualization makes it easier to see how different axis tilts affect the total penetration into the bone, so that this can be minimized. The operator may try different axis tilts and, preferably in real time, see how they affect the maximum and minimum penetration depths. If the tilt of the implant axis A is optimized automatically, the operator may use such a visualization to check the results of the automated procedure, and verify or adjust the selected implant position.

The visualization shown in FIGS. 8a and 8b may also be used by the operator to verify the selected implant template and implant position. This visualization clearly shows the position of a selected implant template at different selected axis tilts.

When a twin implant is to be positioned, the operator preferably first defines the rotation of the twin implant around the axis, since a twin implant is not symmetric around the implant axis A, as a circular implant. The visualization shown in FIG. 4 enables the operator to try different rotations of the twin implant, and see how this affects the maximum and minimum penetration depths of the twin circle of the twin implant. The visualization shown in FIG. 4 shows, preferably in real time, the maximum and minimum penetration for the twin circle of the twin implant at the same time. This visualization makes it easier to manually optimize the tilt of the implant axis. If the tilt of the implant axis is optimized automatically, the operator may use such a visualization to check the results of the automated procedure, and verify or adjust the shape of the resulting twin implant and selected implant position.

The operator preferably positions the virtual implant template so that the implant hat H will at all points be thick enough to ensure mechanical stability, and preferably also thick enough to ensure firm anchoring towards cartilage and bone. One way of doing this is to position the virtual implant template deep enough into the bone that the implant hat H at each point of its circumference penetrates at least a predetermined minimum depth $D_{min}$ into the bone.

The operator may optimize the tilt of the implant axis A by tilting the implant axis A in such a way that the implant nowhere along its circumference penetrates unnecessarily deep into the bone, i.e. minimize the maximum penetration depth $D_{max}$ into the bone along the circumference of the implant hat H. Another way for the operator to optimize the tilt of the implant axis A is to calculate the total volume of bone (and possibly also cartilage) to be removed for implanting the implant, and tilt the implant axis A in such a way that the total volume of bone (and/or cartilage) to be removed for implanting the implant is minimized. Another way is to calculate the surface area of the implant penetration into the bone, and tilt the implant axis A in such a way that the surface area of the implant penetration into the bone is minimized.

Finally, the operator generates 1180 a customized top surface of the implant hat H to correspond to a simulated healthy cartilage surface. The customized top surface of the implant hat H may e.g. be simulated based on the curvature of the cartilage immediately surrounding the area of damaged cartilage. A suitable area comprising and extending around the damaged cartilage may be selected, and the curvature of the whole area simulated in such a way that the curvature of the area which is not damaged matches the simulated curvature. A simulated healthy surface of the area of damaged cartilage may thereby be generated. The simulation may comprise an interpolation, e.g. using the Solid Works Surface Wizard or another suitable tool.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

Further Embodiments

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the claimed scope of the present disclosure. Where applicable, the various hardware components and/or software components set forth herein can be separated into sub-components comprising software, hardware, or both without departing from the claimed scope of the present disclosure. In addition, where applicable, it is contemplated that software components can be implemented as hardware components, and vice-versa. The method steps of one or more embodiments described herein may be performed automatically, by any suitable processing unit, or one or more steps may be performed manually. Where applicable, the ordering of various steps described herein can be changed, combined into composite steps, and/or separated into sub-steps to provide features described herein.

Software in accordance with the present disclosure, such as program code and/or data, can be stored in non-transitory form on one or more machine-readable mediums. It is also contemplated that software identified herein can be implemented using one or more general purpose or specific purpose computers and/or computer systems, networked and/or otherwise.

In embodiments, there are provided a computer program product comprising computer readable code configured to, when executed in a processor, perform any or all of the method steps described herein. In some embodiments, there are provided a non-transitory computer readable memory on which is stored computer readable and computer executable code configured to, when executed in a processor, perform any or all of the method steps described herein.

In one or more embodiments, there is provided a non-transitory machine-readable medium on which is stored machine-readable code which, when executed by a processor, controls the processor to perform the method of any or all of the method embodiments presented herein.

The invention claimed is:

1. A system for optimizing a position of an implant into an anatomical joint of a patient, the system comprising a storage media and a processor, wherein the processor is configured to:
   receive medical image data representing a three dimensional image of the joint from the storage media;
   obtain a three dimensional virtual model of the joint which is based on the received medical image data;
   identify damage in the joint based on the received medical image data and/or the three dimensional virtual model of the joint;
   define an implant area that covers at least a major part of the identified damage;
   position a virtual implant template having an implant hat corresponding to said implant area, in the three dimensional virtual model of the joint; and
   generate a customized top surface of the implant hat to correspond to a simulated healthy cartilage surface;
   wherein the processor is configured to position the virtual implant template by:
      placing the virtual implant template in the three-dimensional virtual model of the joint so that the cross section area of the implant hat in a direction perpendicular to an implant axis covers at least a major part of the damage; and
      optimizing the tilt of the implant axis in the three-dimensional virtual model of the joint, while maintaining the position of the cross section area of the implant hat relative to the three-dimensional virtual model of the joint, by minimizing at least one of:
         the maximum penetration depth $D_{max}$ into the bone along the circumference of the implant hat;
         the total volume of bone and/or cartilage to be removed for implanting the implant; and/or
         the surface area of the implant penetration into the bone.

2. A system according to claim 1, wherein the processor is configured to place the virtual implant template so that the implant hat will at all points be thick enough to ensure mechanical stability, and preferably also thick enough to ensure firm anchoring towards cartilage and bone.

3. A system according to claim 1, wherein the processor is configured to place the virtual implant template so that the implant hat at each point of its circumference penetrates at least a predetermined minimum depth $D_{min}$ into the bone.

4. A system according to claim 1, wherein the implant area has the shape of a circle, or two partly overlapping circles, and the implant hat has the shape of a cylinder, or two partly overlapping cylinders.

5. A system according to claim 1, wherein the processor is configured to restart the optimization of the implant position if at least one predetermined demand on the implant design is not fulfilled.

6. A system according to claim 5, wherein said at least one predetermined demand on the implant design is that the implant hat must have a predetermined minimum thickness $T_{min}$.

7. A method of optimizing a position of an implant into an anatomical joint of a patient, the method comprising:
   receiving medical image data representing a three dimensional image of the joint;
   obtaining a three dimensional virtual model of the joint which is based on the received medical image data;
   identifying damage in the joint based on the received medical image data and/or the three dimensional virtual model of the joint;
   defining an implant area that covers at least a major part of the identified damage;
   positioning a virtual implant template having an implant hat corresponding to said implant area, in the three dimensional virtual model of the joint; and
   generating a customized top surface of the implant hat to correspond to a simulated healthy cartilage surface;
   wherein the positioning involves:
      placing the implant virtual template in the three-dimensional virtual model of the joint so that the cross section area of the implant hat in a direction perpendicular to the implant axis covers at least a major part of the damage; and
      optimizing the tilt of the implant axis in the three-dimensional virtual model of the joint, while maintaining the position of the cross section area of the implant hat relative to the three-dimensional virtual model of the joint, by minimizing at least one of:
         the maximum penetration depth $D_{max}$ into the bone along the circumference of the implant hat;
         the total volume of bone and/or cartilage to be removed for implanting the implant; and/or
         the surface area of the implant penetration into the bone.

8. A method according to claim 7, wherein the positioning involves placing the virtual implant template so that the implant hat will at all points be thick enough to ensure mechanical stability, and preferably also thick enough to ensure firm anchoring towards cartilage and bone.

9. A method according to claim 7, wherein the positioning involves placing the virtual implant template so that the implant hat at each point of its circumference penetrates at least a predetermined minimum depth $D_{min}$ into the bone.

10. A method according to claim 7, wherein the implant area has the shape of a circle, or two partly overlapping circles, and the implant hat has the shape of a cylinder, or two partly overlapping cylinders.

11. A method according to claim 7, wherein if at least one predetermined demand on the implant design is not fulfilled, the optimization of the implant position is restarted.

12. A method according to claim 11, wherein said at least one predetermined demand on the implant design is that the implant hat must have a predetermined minimum thickness $T_{min}$.

13. A method according to claim 7, wherein the anatomical joint is a knee, an ankle, a hip, a toe, an elbow, a shoulder, a finger or a wrist.

14. A non-transitory machine-readable medium on which is stored machine-readable code which, when executed by a processor, controls the processor to perform the method steps of claim 7.

15. The method of claim 7, further comprising generating a model of the joint with the implant to enable determining whether the implant matches surrounding surfaces of the joint.

16. The system of claim 1, wherein the processor is further configured to generate a model of the joint with the implant to enable determining whether the implant matches surrounding surfaces of the joint.

* * * * *